United States Patent
Augustine et al.

(12) 
(10) Patent No.: US 6,235,047 B1
(45) Date of Patent: *May 22, 2001

(54) WOUND TREATMENT APPARATUS WITH A HEATER, A HEAT CONDUCTIVE BANDAGE, AND HEAT-SPREADING MEANS ACTING BETWEEN THE HEATER AND BANDAGE

(75) Inventors: Scott D. Augustine, Bloomington; Keith J. Leland, Plymouth; John P. Rock; Donald E. Stapf, both of Minneapolis, all of MN (US)

(73) Assignee: Augustine Medical, Inc., Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/056,191

(22) Filed: Apr. 6, 1998

(51) Int. Cl.[7] ........................................ A61F 7/00
(52) U.S. Cl. .................... 607/96; 602/2; 602/14; 602/42
(58) Field of Search .................... 602/2, 14, 40, 602/42, 54, 57; 604/113, 144; 607/96, 108–112, 114

(56) References Cited

U.S. PATENT DOCUMENTS

| | | | |
|---|---|---|---|
| 3,867,939 | * | 2/1975 | Moore et al. ............................. 602/2 |
| 5,662,624 | * | 9/1997 | Sundstrom et al. ..................... 602/2 |
| 5,817,145 | * | 10/1998 | Augustine et al. ..................... 607/96 |

FOREIGN PATENT DOCUMENTS

94/00090 * 1/1994 (WO) .................................. 607/112

* cited by examiner

Primary Examiner—Robert L. Nasser
(74) Attorney, Agent, or Firm—Gray Cary Ware & Freidenrich

(57) ABSTRACT

A wound treatment apparatus is provided which includes a thermally conductive bandage, a heater in thermal contact with the bandage over a wound treatment area, a heat spreading means acting between the heater and the bandage for laterally spreading heat transferred from the heater to the bandage in order that heat be substantially uniformly distributed across the bandage.

16 Claims, 13 Drawing Sheets

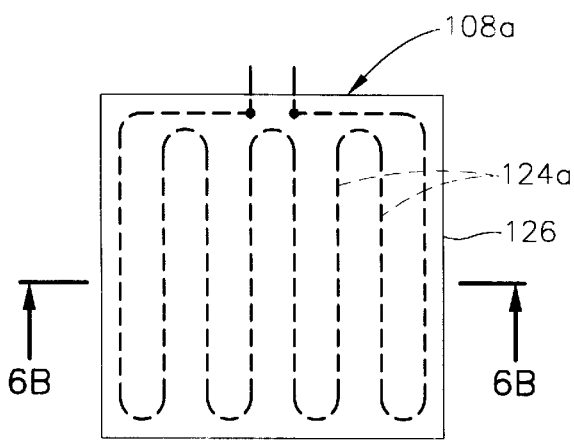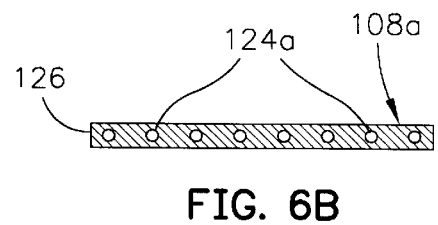
FIG. 6A  FIG. 6B
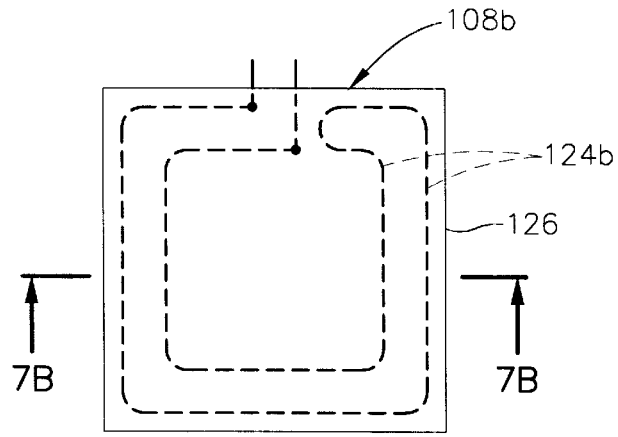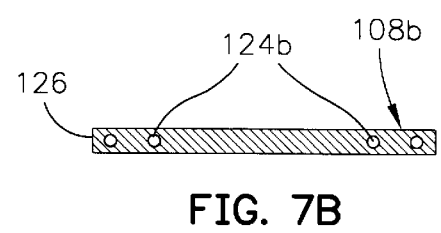
FIG. 7A  FIG. 7B
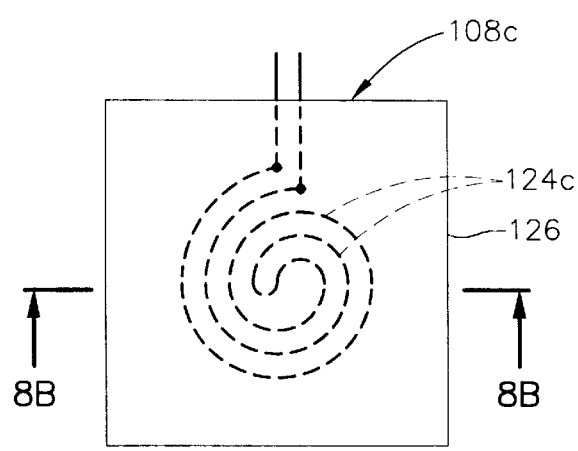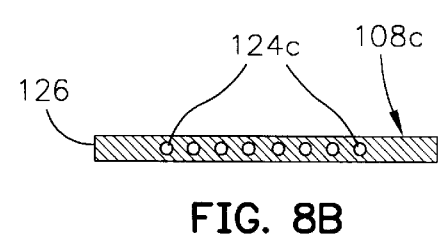
FIG. 8A  FIG. 8B

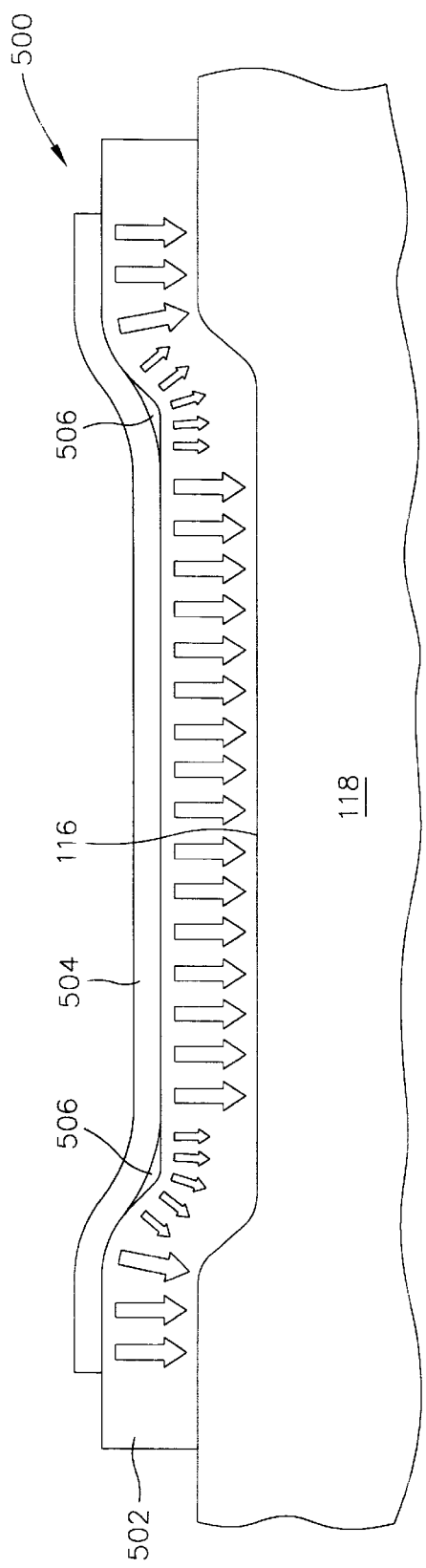
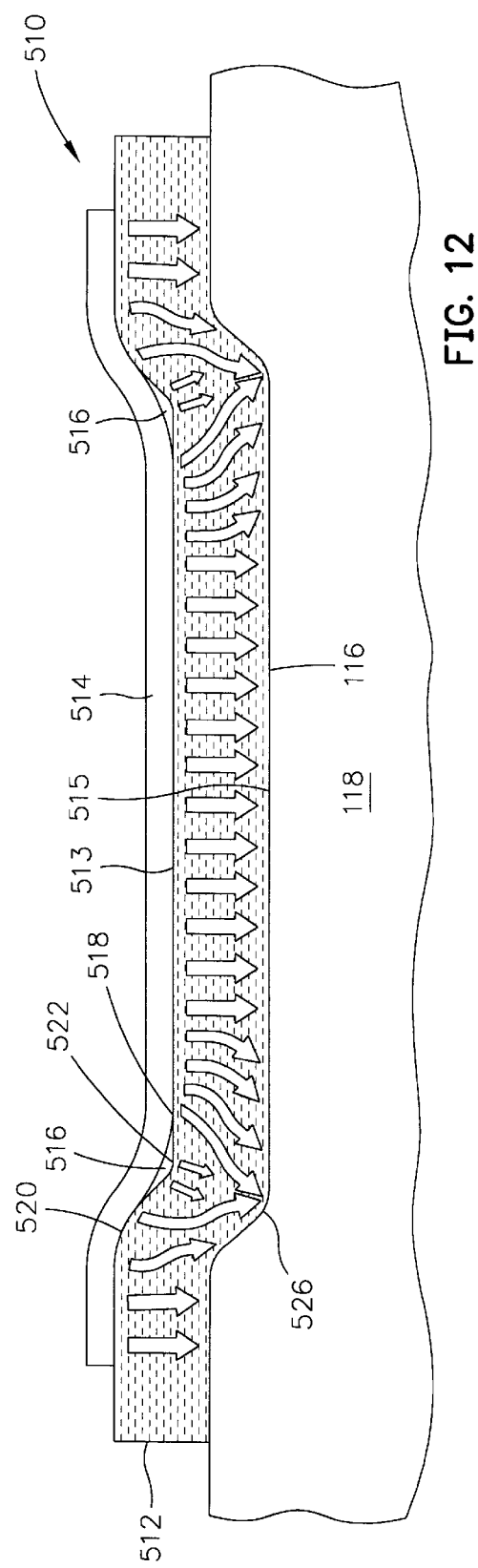

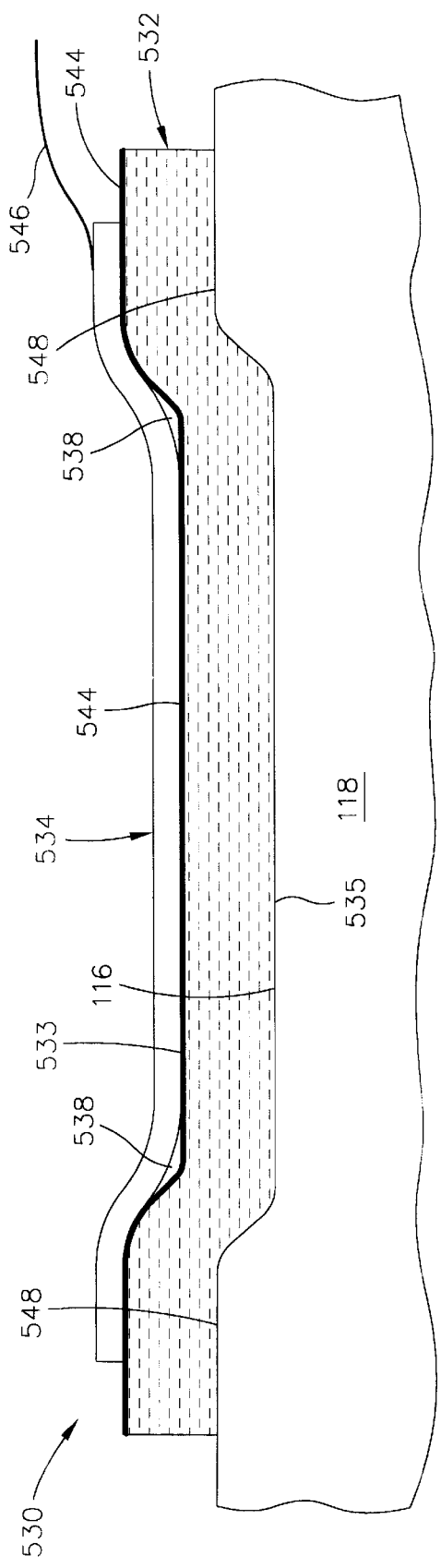
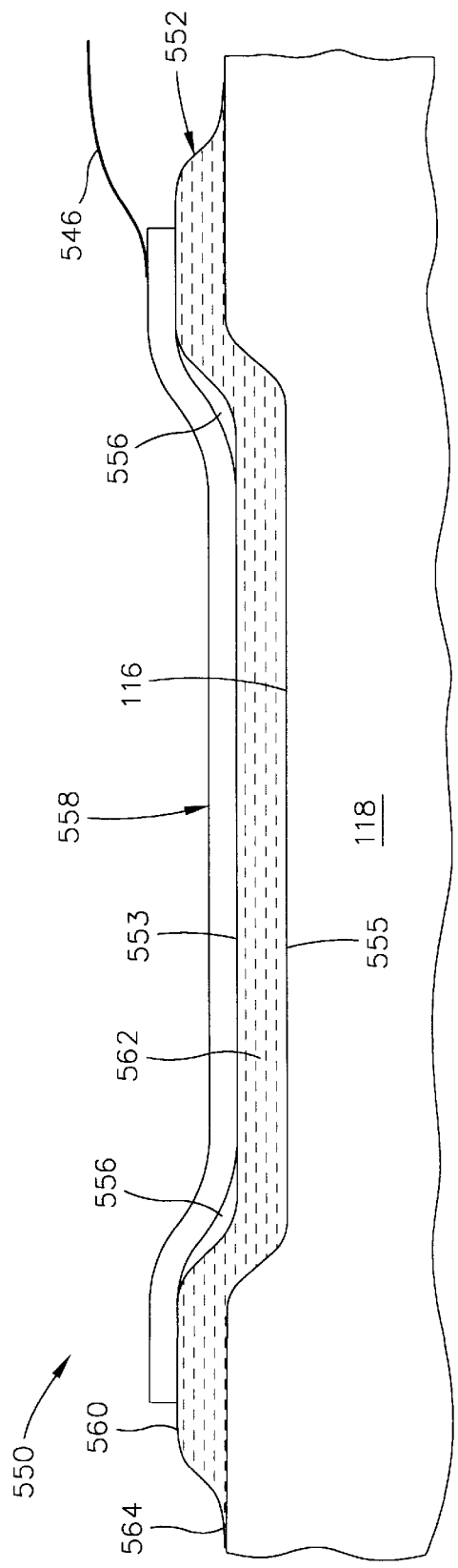
FIG. 13
FIG. 14

WOUND TREATMENT APPARATUS WITH A HEATER, A HEAT CONDUCTIVE BANDAGE, AND HEAT-SPREADING MEANS ACTING BETWEEN THE HEATER AND BANDAGE

CROSS-REFERENCES TO RELATED PATENT AND COPENDING APPLICATIONS

This application contains material related to U.S. patent application Ser. No. 08/843,072 filed on Apr. 11, 1997 entitled "FLEXIBLE NON-CONTACT WOUND TREATMENT DEVICE WITH A SINGLE JOINT" and to the following commonly assigned pending U.S. patent applications:

Ser. No. 07/900,656, filed Jun. 19, 1992, for "THERMAL BODY TREATMENT APPARATUS AND METHOD";

Ser. No. 08/342,741, filed Nov. 21, 1994, for WOUND TREATMENT DEVICE";

Ser. No. 08/356,325, filed Feb. 21, 1995, for "WOUND COVERING";

Ser. No. 08/785,794, filed Jan. 21, 1997, for "NORMOTHERMIC HEATER WOUND COVERING";

Ser. No. 08/786,713, filed Jan. 21, 1997, for "NORMOTHERMIC TISSUE HEATING WOUND COVERING";

Ser. No. 08/786,714, filed Jan. 21, 1997, for "NEAR HYPOTHERMIC HEATER WOUND COVERING"; and Ser. No. 08/838,618, filed Apr. 11, 1997, for "FLEXIBLE NONCONTACT WOUND TREATMENT DEVICE".

This application also contains material related to the following commonly assigned U.S. patent applications, which were concurrently filed with this application:

Ser. No. 09/065,597 filed Sep. 6, 1998 for "WOUND TREATMENT APPARATUS WITH A HEATER ADHESIVELY JOINED TO A BANDAGE";

Ser. No. 09/055,725 filed Apr. 6, 1998 for "WOUND TREATMENT APPARATUS WITH INFRARED ABSORPTIVE WOUND COVER";

Ser. No. 09/056,063 filed Apr. 6, 1998 for "WOUND TREATMENT APPARATUS WITH IR TRANSPARENT OR IR TRANSMISSIVE WOUND COVER"; and Ser. No. 09/055,605 filed Apr. 6, 1998 for "WOUND TREATMENT APPARATUS FOR NORMOTHERMIC TREATMENT OF WOUNDS".

STATEMENT OF REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

1. Field of the Invention

The present invention relates to a wound treatment device with a bandage and heater that are preferably planar, yet flexible, and are connected or joined in a manner that promotes substantially uniform heat transfer from the heater to, and through, the bandage.

2. Description of the Related Art

Wounds, in general, are breaks in the integrity of the skin of a patient. A first type of wound may result from mechanical trauma that produces a cut, tear, or an abrasion. There are many instruments of causality for such wounds, including knives, glass, gravel, or a scalpel. A second type of wound may be caused by a combination of heat and pressure, where the heat alone is insufficient to cause an outright burn. Such wounds include pressure sores, decubitus ulcers, or bed sores, and reflect an injury that is chronic in nature. A wound may also be vascular in origin. In this third type of wound, blood flow through a region may be altered sufficiently to cause secondary weakening of tissues, which are eventually disrupted, thus forming a wound. In the case of arterial causes, the primary difficulty is getting oxygenated blood to the affected area. For venous causes, the primary difficulty is fluid congestion in the affected area, which backs up, decreasing the flow of oxygenated blood. Because these wounds manifest underlying chronic disease processes, such as atherosclerotic vascular disease, congestive heart failure, and diabetes, these vascular injuries also are chronic in nature, forming wounds with ulcerated bases.

Heat therapy has been used to treat wounds since the days of Hippocrates, with varying results. Up to now, heat therapy for wounds has involved the application of heat under conditions that make the tissues of a wound hyperthermic. Hyperthermia impedes wound healing and may actually damage the wound tissues.

The "normal" range of temperature for the human body is 37° C.±1° C. (36° C.–38° C.). This is termed the "normothermic" range. Humans exhibit a thermoregulatory response to core temperature changes as little as ±0.1° C., wherein "core" as used herein refers to interior portions of the body. This extremely tight temperature control is necessary because virtually all cellular functions, chemical reactions and enzymatic reactions are optimum at normothermia.

Surface tissue varies in temperature according to where on the body it is located. The skin of the torso is usually hypothermic, while the skin of the legs is always hypothermic. The normal skin temperature of the distal leg is approximately 32° C., which is considered to be "moderately hypothermic". The skin temperature of the distal leg of a patient with vascular insufficiency may be as low as 25° C., which is "severely hypothermic". The hypothermic condition of wounds and ulcers inhibits healing. Severely hypothermic skin or wound tissue is in a state that may be termed "suspended animation". In suspended animation, tissue is living, but cellular functions necessary for cell division and collagen deposition are slowed or even stopped. Further, the immune system is inhibited, allowing wounds to become heavily colonized with bacteria. The local application of heat to hypothermic skin will cause some degree of vasodilatation, resulting in an increase in local blood flow. Increased blood flow increases the subcutaneous oxygen tension ($PsqO_2$) which, in turn, increases collagen deposition and enhances immune function.

Many references report that the immune system is inhibited by hypothermia and activated by mild hyperthermia (fever). Persp Biol Med:439–474, Spring 1980, reports that local body temperature is a critical factor determining host susceptibility, the location of lesions and contracting infectious diseases. New Eng J Med 305:808–814, 1981, reports that animals exposed to cold environments are more susceptible to infectious diseases, whereas exposure to high ambient temperatures often produces a beneficial result. Wound Rep Reg 2:48–56, 1994 and Acta Anaesth Scand 38:201– 205, 1994, report that infections caused by a standard inoculum of e. coli or s. aureus were significantly more severe in hypothermic guinea pigs than in normothermic control animals. New Eng J Med 334:1209–1215, 1996, reports that hypothermic colorectal surgical patients had three times more wound infections (19% vs. 6%) than those who were kept normothermic during surgery with a Bair Hugger® patient warming system described in commonly assigned U.S. Pat. Nos. 5,324,320, 5,300,102 and 5,350,417. Further, six weeks of warming therapy with the Bair Hugger® patient warming system has successfully healed chronic progressive ulcers which heretofore have been resistant to standard therapies.

Currently available medical devices that apply heat to wounds include infrared lights, warm water pads, warm water bottles, whirlpools and Sitz baths. All types of lesions, such as surgical, chronic, traumatic, donor sites, infected wounds and burns, have been treated with these warming modalities. Particularly difficult has been the application of heat to open wounds such as ulcers. Treatment of a wound with infrared light requires that the wound be positioned under the light during therapy, necessitating patient immobility. Further, the infrared heat causes the wound to dry, thereby slowing the healing process. Warm water pads and bottles and electrical heating pads are cumbersome, reduce patient mobility, and are usually applied to the extremities and held in place with inconvenient wraps such as straps, hook-and-eye material or tabs. Whirlpools and Sitz baths reduce mobility and limit the duration of warming therapy due to skin maceration by the water. None of these modalities is capable of prolonged heat treatment of a wound.

SUMMARY OF THE INVENTION

There is a need for a wound treatment apparatus to treat a wound with uniformly applied heat for a prolonged period of time, while promoting patient convenience and mobility. Preferably, the heat should produce a substantially normothermic condition in the tissues in and near the wound. It is also important that the wound treatment apparatus be flexible and have a low profile for convenience of the patient. Such a wound treatment apparatus should efficiently and uniformly transfer heat, be convenient to operate without adversely impacting the patient, and be capable of maintaining a moist wound environment.

Preferably, the placement of the wound treatment apparatus is referred to a "wound treatment area" (or "treatment area") that may include the wound, unwounded skin adjacent the wound (the periwound), or both.

This invention accomplishes the goal of efficient provision of uniform heat to the tissue of a wound treatment area in a unique and practical way. The invention includes three parts: a thermally conductive bandage; a heater which is attachable to the bandage; and a heat spreading means acting between the bandage and the heater for laterally spreading heat from the heater so that the heat is substantially uniformly distributed across the bandage. As a result, the bandage provides heat to the tissue of a wound treatment area that is substantially uniformly spread across the tissue. The heat spreading means may be a distinct member that is separate from the bandage and the heater. Alternately, the heat spreading means may be incorporated into the structure of the bandage.

An object of the present invention is to provide a wound treatment apparatus for treating wounds with heat which has a low profile for convenience of a patient, is flexible for mobility of the patient and uniformly transfers heat to a wound and/or periwound site so as to promote normothermic treatment thereof.

Another is to provide a substantially planar wound treatment apparatus that conforms to the wound and the adjacent skin.

A further object is to provide a low profile and flexible wound treatment apparatus that promotes uniform heat transfer to a wound and is easy to operate without impacting the patient's comfort.

Still a further object is to provide a highly mobile and convenient wound treatment apparatus which promotes uniform heat transfer to a wound and which maintains a moist environment thereon.

Other objects and advantages of the invention will become apparent upon reading the following description taken together with the accompanying drawings.

DESCRIPTION OF THE DRAWINGS

FIG. 6A is a planar illustration of an electrical resistance element embedded in a flexible layer for uniform heating;

FIG. 6B is a view taken along plane VIB—VIB of FIG. 6A;

FIG. 7A is a planar view of an electrical resistance element embedded in a flexible layer for heating a portion of a treatment area;

FIG. 7B is a view taken along plane VIIB–VIIB of FIG. 7A;

FIG. 8A is a planar view of an electrical resistance element embedded in a flexible layer for uniform heating of a central portion of a treatment area;

FIG. 8B is a view taken along plane VIIIB–VIIIB of FIG. 8A;

FIG. 11 is a cross-sectional drawing of a prior art wound treatment apparatus in which heat is transferred to a bandage primarily by convection;

FIG. 12 is a cross-sectional drawing of a wound treatment apparatus according to this invention in which heat is substantially uniformly distributed throughout a bandage;

FIG. 13 is a cross-sectional drawing of the wound treatment apparatus of FIG. 12 with a polymeric film;

FIG. 14 is a cross-sectional drawing of another embodiment of a wound treatment apparatus according to this invention;

DESCRIPTION OF THE PREFERRED EMBODIMENTS

Wound Treatment Apparatus

Figure 1:
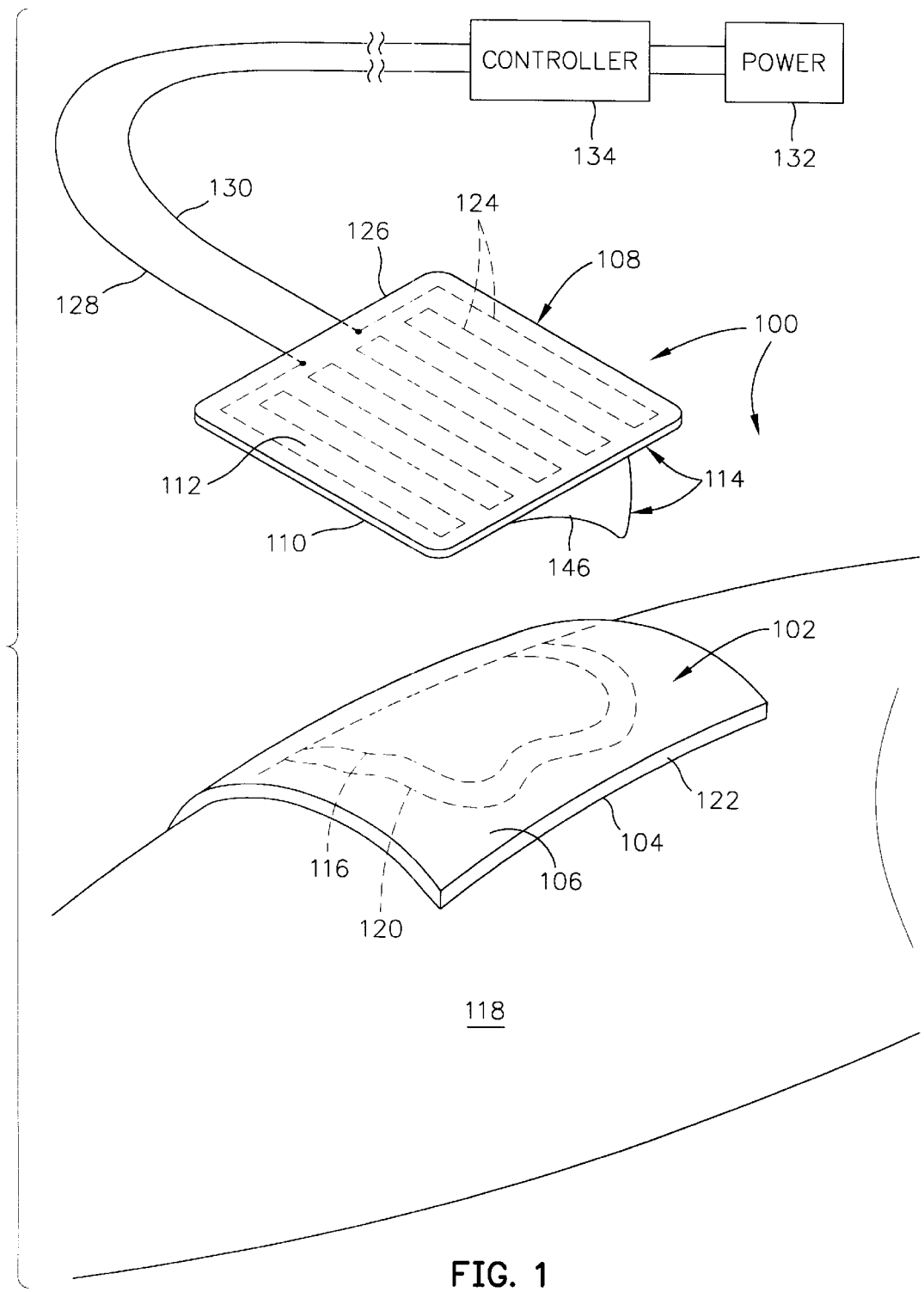
FIG. 1 is an isometric view of a wound treatment apparatus being applied to a wound on a person's body.
Figure 2:
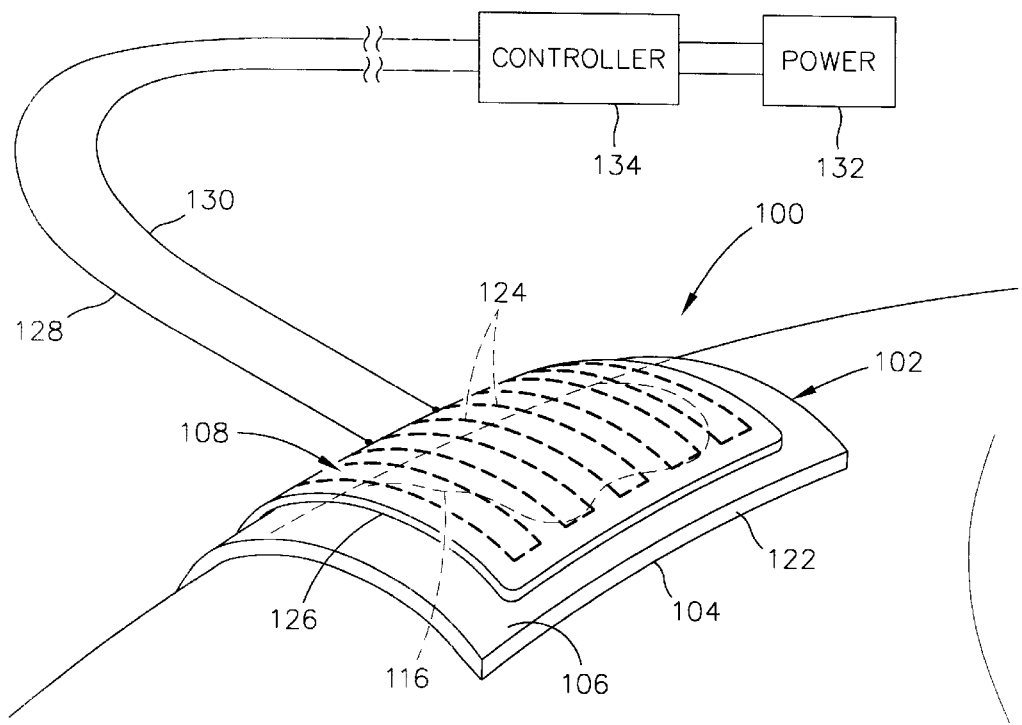
FIG. 2 is an isometric view of the wound treatment apparatus applied to the wound on the person's body.
Figure 3:
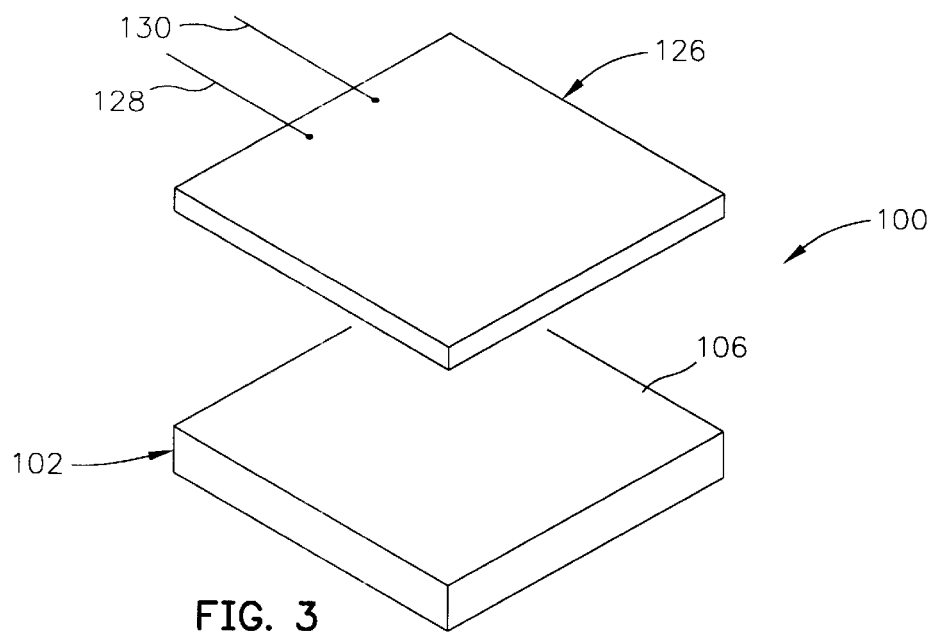
FIG. 3 is an exploded isometric view of the wound treatment apparatus.
Figure 4:
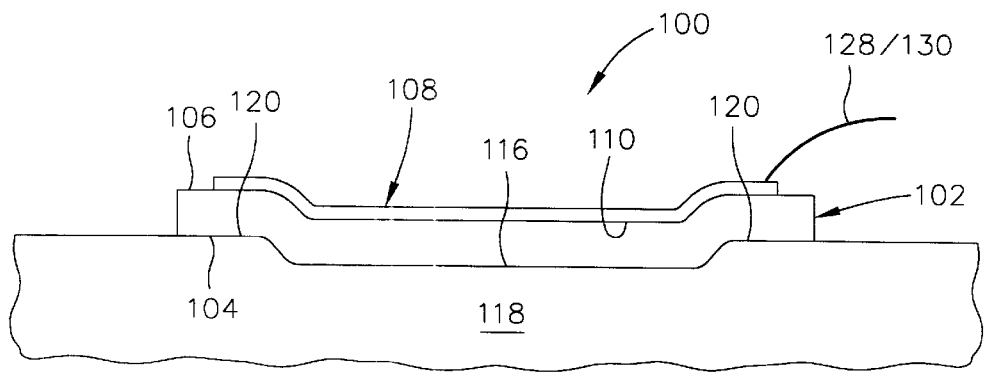
FIG. 4 is a cross-sectional view of the wound treatment apparatus applied to the wound on the person's body.

As shown in FIGS. 1–5, a wound treatment apparatus 100 includes a thermally conductive bandage 102 which has first (lower) and second (upper) surfaces 104 and 106, a heater 108 which has first (lower) and second (upper) surfaces 110 and 112 and means 114 for joining the heater 108 and the bandage 102 in such a manner as to transfer heat from the heater 108 to the bandage 102. In FIGS. 2 and 4, the wound treatment apparatus 100 is shown in place covering a wound 116 of a person's body 118, the wound being shown depressed. Immediately adjacent the wound is a periwound area 120 which is typically a peripheral band of tissue around the wound area with less trauma than the tissue of the wound area. As will be explained in more detail hereinafter, the wound treatment apparatus is capable of treating a wound treatment area that includes the wound and/or the periwound area, as desired.

The second surface 106 of the bandage preferably comprises a sheet of smooth material. This surface may be provided by a polymeric film. A layer 122 of hydrogel, hydrocolloid, or hydrated alginate may be affixed to the polymeric film 106 by any suitable means, such as an adhesive, and may provide the first surface 104. Any of these combinations provide the bandage with high thermal conductivity and maintain a moist environment at the wound. In the layer 122, a foam or gauze may be used in lieu of the compounds enumerated above. If the gauze or foam provides the first surface 104, the gauze or foam will absorb moisture from the wound, providing the desired heat conductivity and moist environment. Alternatively, the bandage 102 may simply be a single layer or film of a heat-conductive polymer so as to optimize heat conductivity of the bandage. Preferably, the bandage is planar, as shown in FIG. 3, and flexible, so as to conform to the wound 116 as shown in FIG. 4, as well as to the person's body, as shown in FIGS. 1 and 2.

In the wound treatment apparatus 100, the heater 108 includes means for generating heat that may be electrically operated. For example, the means may take hte form of an electrical resistance element 124 which is embedded in or laminated to a flexible planar member 126, such as polyethylene, silicon, rubber or flexible cloth. Preferably, the heater 108 is substantially planar, as shown in FIGS. 1 and 3, and yet flexible in order that it conform, with the bandage, to the wound 116, as shown in FIG. 4, and to the person's body as shown in FIGS. 2 and 4.

As illustrated in FIGS. 1, 2 and 4, the electrical resistance element 124 is connected to first and second electrical conductors 128 and 130, which are connected to an electrical power source 132, via a controller 134. The purpose of the controller 134 is to control electrical power provided to the electrical resistance element 124 to maintain a normothermic environment at the wound 116. As shown in FIGS. 1 and 2, the electrical resistance element 124 may extend back and forth in the flexible planar member 126 with a desired spacing to promote uniform heating of the bandage 102.

Figure 5:
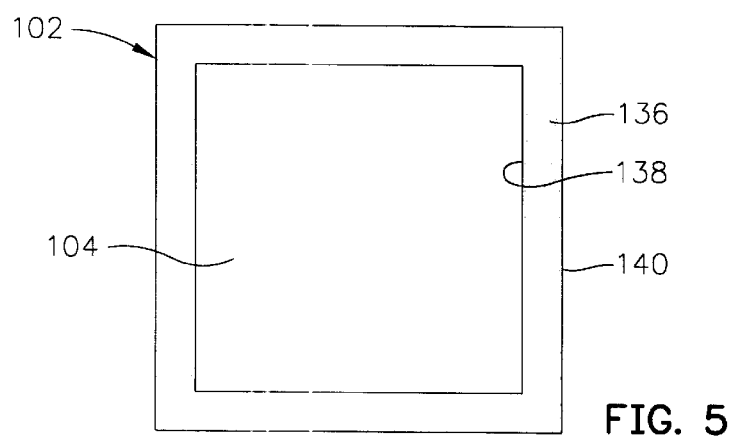
FIG. 5 is a plan view of the bottom surface of a bandage in the wound treatment apparatus of FIGS. 1–4.

As shown in FIG. 5, the first surface 104 of the bandage 102 is provided with a pattern of adhesive material 136 at or near its periphery. Preferably, the adhesive pattern 136 is closed so that it may encompass the wound and the peri-wound area and trap the natural moisture of the body which, in turn, moistens the layer 122 of the bandage, or otherwise maintains a moist environment across the wound treatment area for wound therapy purposes. Accordingly, the pattern of adhesive 136 has inner and outer boundaries 138 and 140 wherein the outer boundary 140 coincides with the outer perimeter of the bandage. It should be understood that the bandage 102, the heater 108, and the pattern of adhesive 136 may take various shapes, such as the square, shown in the drawings, or a rectangle, circle or ellipse, or any other regular or irregular shape, depending upon various shapes of wound treatment areas.

FIGS. 6–8 illustrate various electrical resistance heaters 108. In the heater 108a shown in FIG. 6A, and electrical resistance element 124a winds back and forth within the flexible planar member 126, similar to what is shown in FIG. 1. The spacing between the windings of the electrical resistance element 124a may be sized so as to ensure substantially uniform heating. FIG. 6B shows the electrical resistance element embedded or laminated in the flexible planar member 126. In FIG. 7A, the electrical resistance element 124b takes a path along a peripheral zone of the flexible planar member 126, so that the periphery of the heater 108b is uniformly heated to a temperature greater than a central portion of the heater. Again, these electrical resistance elements 124b are shown embedded or laminated in the flexible planar member 126 in FIG. 7B. In FIGS. 8A and 8B, the electrical resistance element 124c takes a spiral path out and back within a central region of the heater 108c so as to uniformly heat the central region of the heater to a higher temperature than regions outbound therefrom. The heater 108a is adapted for applying heat to both the wound and periwound area 116 and 120 in FIG. 4, the heater 108b is adapted for applying heat primarily to the periwound area 120 and the heater 108c is adapted for applying heat primarily to the wound 116.

Figure 9:
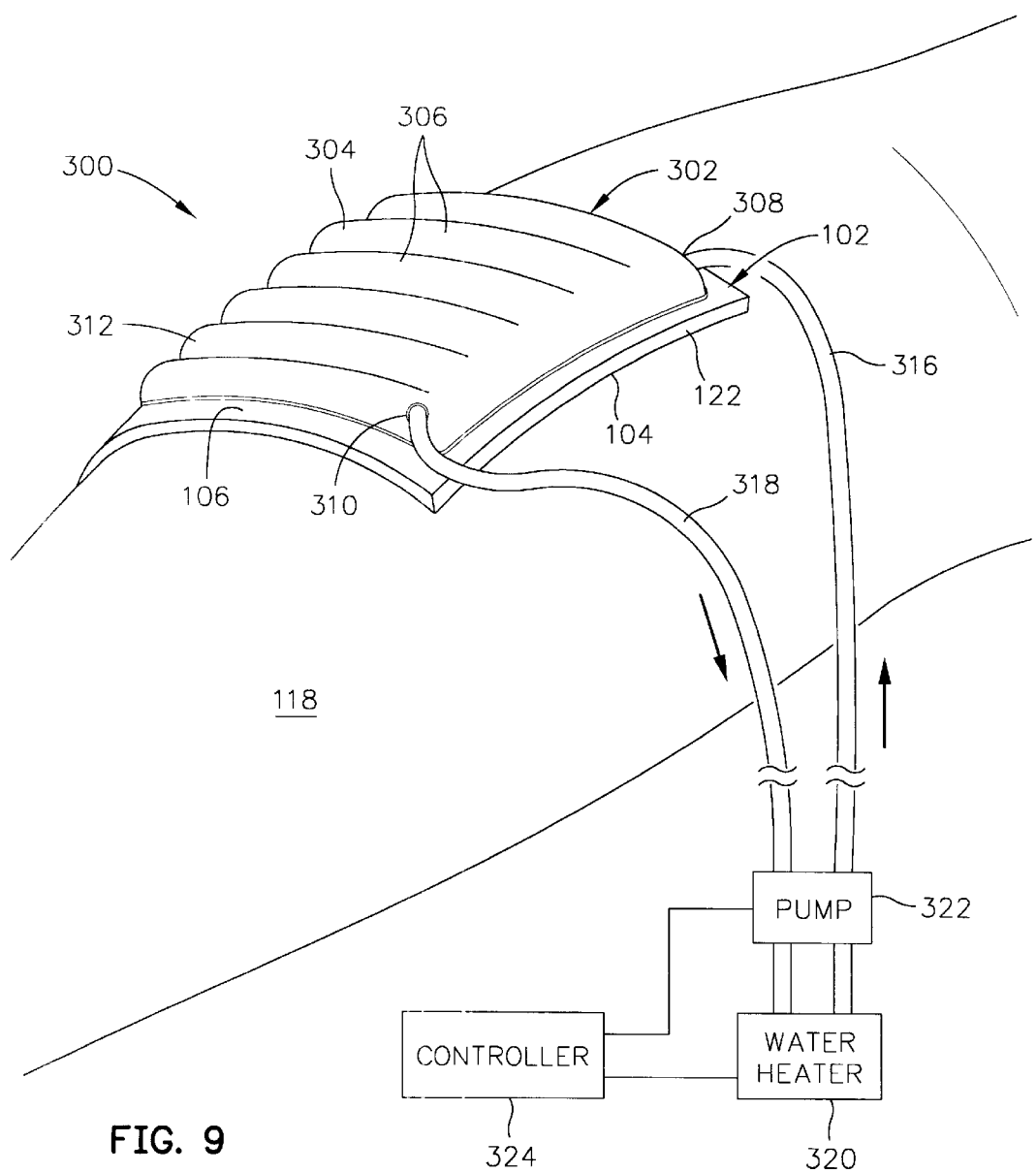
FIG. 9 is an isometric illustration of a wound treatment apparatus with a hot water heater.

Another wound treatment apparatus 300 is illustrated in FIG. 9. In this apparatus, a heater 302 employs heated water as the means for generating heat to be applied to the bandage 102 and then to a wound site covered by the bandage. The heater 302 may comprise a pouch 304 which has water channels 306 extending back and forth in series from an inlet end 308 to an outlet end 310. The pouch 304 may be made by thermo-setting the periphery as well as channel lines of a pair of polymeric films. The bottom film may be stiffer than the top film 312. Heated water is supplied by inlet and outlet water lines 316 and 318 which are connected to a water heater 320 via a pump 322. A controller 324 is provided for controlling the temperature of the water in the water heater 320 and the amount of water pumped by the pump 322. The heated water is preferably maintained at such a temperature and flow rate that the wound site 116 is maintained at a normothermic temperature.

Figure 10:
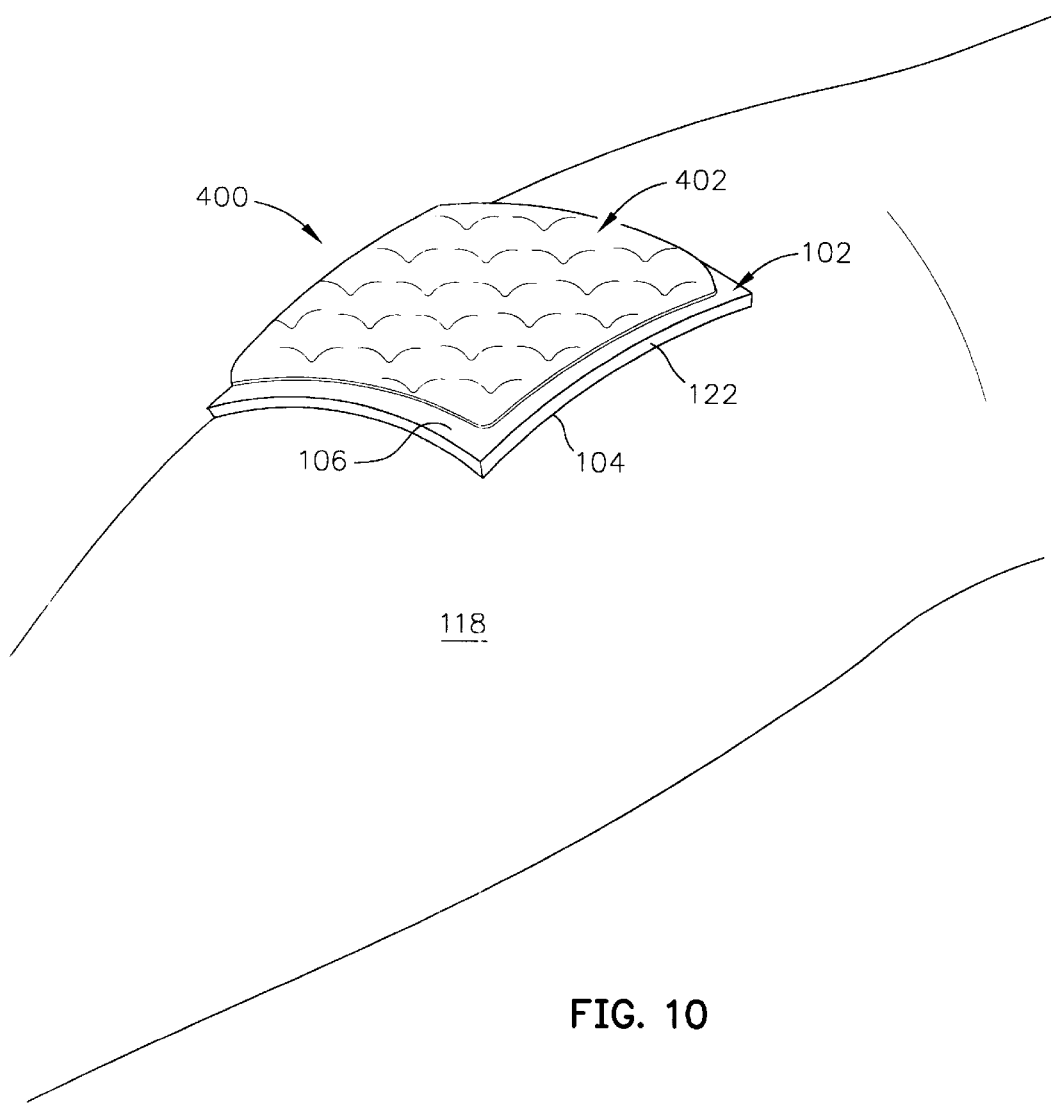
FIG. 10 is an isometric illustration of a wound treatment apparatus with a chemical heater.

Still another wound treatment apparatus 400 is illustrated in FIG. 10. In this apparatus a heater 402 employs a chemical or phase-change salt as the means for heat to be applied to the bandage 102. The heater 402 may comprise a pair of polymeric films which are sealed at their peripheries to provide an enclosure for the chemical or phase change salt. Further, the polymeric films may be joined by spot thermo-setting at spaced-apart locations for the purpose of lowering the profile of the heater and maintaining the chemical or phase-change salt in discrete confined areas. One film may be stiffer than the other film.

FIG. 11 is a cross-section of a wound treatment apparatus 500 that employs a bandage 502 that does not exhibit heat spreading characteristics, shown schematically for explaining its operation. Heat is transmitted to the bandage 502 by a heater 504 and the bandage 502, in turn, conducts heat to the wound site 116. The heater 504 makes contact with an upper surface of the bandage 502 so that heat is transmitted by conduction between the heater 504 and the bandage 502 where the devices are in contact. When the wound treatment apparatus is applied to a person's body, the bandage 502 will assume the contours of the person's body, which may include a depressed wound site. This typically causes gaps 506 between the heater 504 and the upper surface of the bandage 502. The bandage 502 is shown as having poor heat transfer ability at the gaps 506 which causes little heat to be received and conducted by the bandage, as shown by the small arrows. This is in contrast to a larger amount of heat conducted through the bandage, as shown by the large arrows, where the heater 504 contacts the upper surface of the bandage 502. This results in non-uniform heat distribution at the wound site 116, which can cause portions of the wound site to receive unsatisfactory heat therapy.

The Invention

The invention employs a heat spreading means acting between a heater and a thermally conductive bandage. The heat spreading means receives heat from the heater, spreads the heat latterally with respect to the lower surface of the heater and the lower surface of the bandage, and provides the heat to the bandage with a substantially uniform distribution across the bandage. The heat spreading means may be in the structure of the bandage itself and thus may be part of the bandage. The heat spreading means may also be an element that is physically separate from the bandage.

FIG. 12 shows a cross-section of a wound treatment apparatus 510 which employs a bandage 512, with arrows showing the heat received and conducted therethrough. The bandage 512 has an upper surface 513 and a lower surface 515. The heater 514 makes contact with the upper surface 513 of the bandage 512 with the exception of gaps 516 between the heater and the upper surface of the bandage 512 due to contour of the wound site 116. The bandage 512 is made of a thermally conductive material that is thick enough to permit heat at spaced apart contact regions 518 and 520, adjacent a non-contact region 522 at the upper surface of the bandage, to flow by conduction from the upper surface 513 and to substantially merge at 526 at the lower surface 515 of the bandage 512. With this arrangement, the lack of heat conduction at the gaps 516 can be overcome by lateral conduction of the heat within the bandage 512 due to the conductive material and the thickness of the bandage 512. This results in a substantially uniform distribution of heat across the lower surface 515.

A wound treatment apparatus 530 shown in FIG. 13 includes an embodiment 532 of the thermally conductive bandage of FIG. 12. The bandage 532 includes an upper surface 533 and a lower surface 535. The bandage 532 and a heater 534 are shown depressed within the wound site 116 causing gaps 538 between the heater 534 and the bandage 532. The bandage 532 is fabricated from thermally conductive material sufficiently thick that heat introduced at the upper surface 533 may spread laterally in the bandage 532 and may be provided at the lower surface 535 with a substantially uniform distribution across that surface, as the embodiment shown in FIG. 12. In this embodiment the material of which the bandage 532 is made includes a thermally-conductive fluid, such as a hydrated material. Preferred materials include hydrogels and hydrocolloids. It is preferred that the top surface of the bandage 532 comprise a polymeric film 544. The polymeric film 544 serves a double function: retention of fluid or water within the bandage 532, and provision of a surface for attaching the heater 534 to the top surface of the bandage 532 with an adhesive. The heater 534 may be electrically operated and may receive its power from a power supply and controller via leads 546 for maintaining a normothermic temperature at a wound treatment area. The heater 534 also comprise other means of generating heat. In this embodiment, the bandage 532 essentially forms a heat spreading layer.

FIG. 14 is a cross-section of a wound treatment apparatus 550 which employs a second embodiment 552 of a thermally conductive bandage. The bandage has an upper surface 553 and a lower surface 555. The wound treatment apparatus 550 is depressed in the wound 116, which causes gaps 556 between the heater 558 and the bandage 552. The bandage 552 is a flexible pouch 560 which is filled with a thermally conductive fluid such as water 562. The pouch may be made from polymeric films which are sealed around a periphery 564. The depth of the fluid in the pouch is such that heat that is conducted from the upper surface 553 to the lower surface 555 spreads laterally throughout the bandage 552 so that it is substantially uniformly distributed across the lower surface 555. The bandage 552 in essence forms a heat spreading layer.

Figure 15:
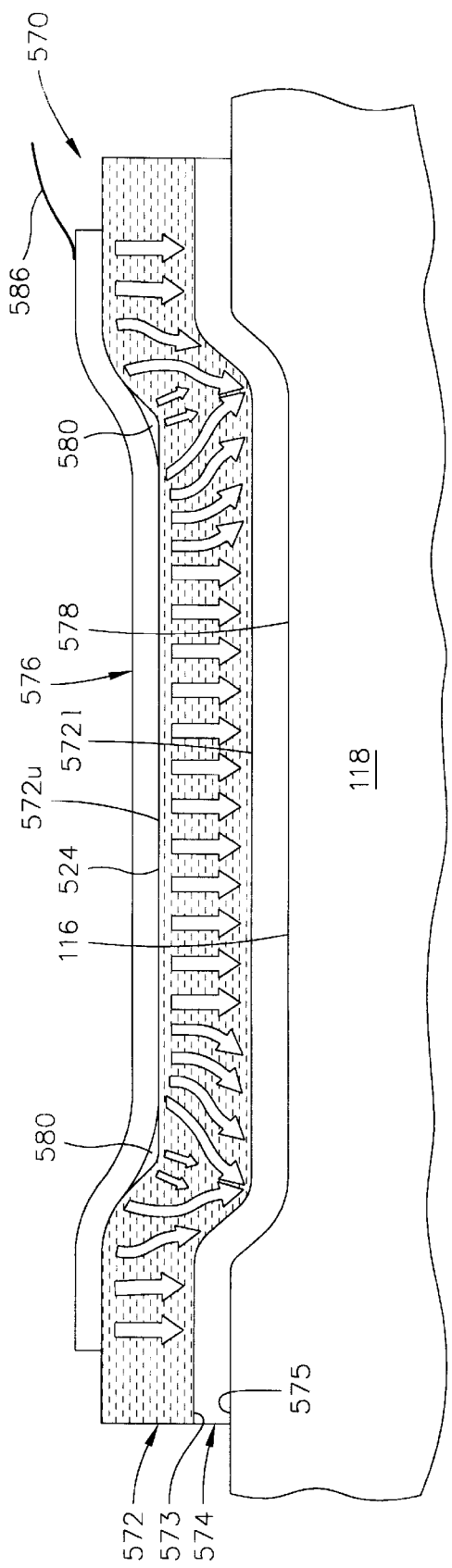
FIG. 15 is a cross-sectional drawing of another embodiment of wound treatment apparatus according to this invention.

FIG. 15 shows a cross-section of a wound treatment apparatus 570 that employs a separate heat spreading layer 572 sandwiched between a bandage 574 and a heater 576, the heat spreading layer 572 being shown schematically with arrows for explaining the heat within the heat spreading layer. The heat spreading layer 572 includes an upper surface 572u and a lower surface 572l. The bandage 574 includes an upper surface 573 and a lower surface 575. The wound treatment apparatus 570 is shown depressed in a wound 116, with gaps 580 formed between the heater 576 and the heat spreading layer 572. The heat spreading layer 572 is made of a material with high thermal conductivity, while the bandage 574 is made of a material with low thermal conductivity, such as gauze. Accordingly, the heat spreading layer 572 is employed for laterally spreading the heat adjacent the gaps 580 from the upper surface 572u to the lower surface 572l of the heat spreading layer 572 so that the heat is substantially uniformly distributed across the upper surface 573 of the bandage 574, as shown by the large arrows. Because of the nature of the material of which the bandage 574 is made, the heat remains substantially uniformly distributed through the bandage 574 and across the lower surface 575.

Figure 16:
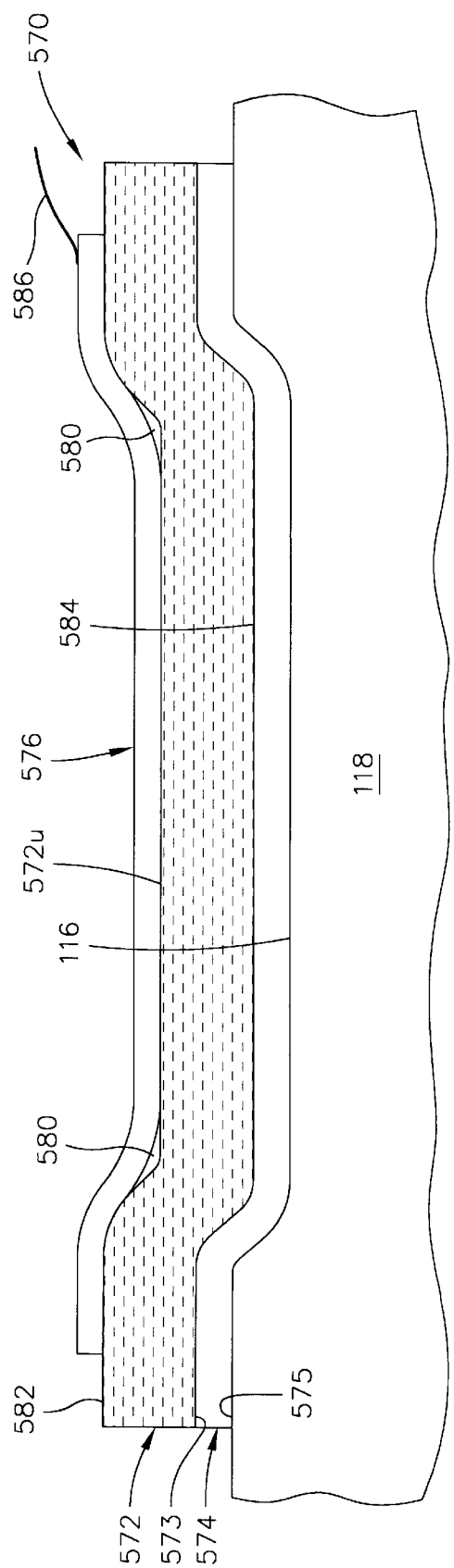
FIG. 16 is a cross-sectional drawing of the FIG. 15 embodiment of the wound treatment apparatus showing a polymeric film.

In FIG. 16 the wound treatment apparatus 570 is shown without the arrows. A fluid containing material such as a hydrated material may be employed for the heat spreading layer 572. Suitable materials are hydrogels and hydrocolloids. In this case, the heat spreading layer 572 may optionally be provided with a thin polymeric film 582 applied to the upper surface 572u for retaining fluid within the heat spreading layer, as well as for providing adhesion between the heater 576 and the heat spreading layer 572. It is preferred that the heat spreading layer 572 and the bandage 574 be made as one component, with the heat spreading layer 572 and the bandage 574 having a common layer 584 therebetween. This will ensure that there are no gaps between the heat spreading layer 572 and the bandage 574. The heater 576 may be electrically actuated, or may comprise a non-electric means for generating heat.

Figure 17:
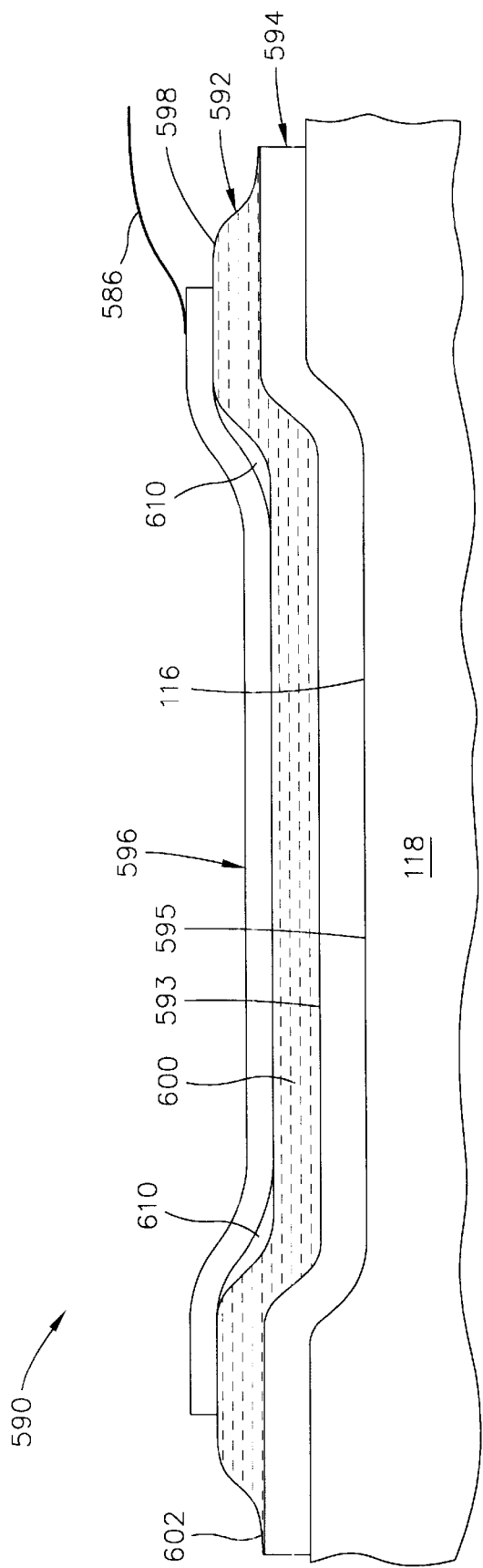
FIG. 17 is a cross-sectional drawing of another embodiment of a wound treatment apparatus according to this invention.

FIG. 17 shows a cross-section of a wound treatment apparatus 590 which employs a separate heat spreading layer 592 between a bandage 594 and a heater 596. In this embodiment the heat spreading layer 592 is a pouch 598 which contains a heat conductive fluid such as water 600. The pouch is formed on the upper surface 593 of the bandage 594. Similar to the pouch 560 described in FIG. 14 the pouch 598 may comprise polymeric films which are sealed at a periphery 602. Because of the depression of the wound 116, there are gaps 610 between the heater 596 and the heat spreading layer 592. The depth or thickness of the fluid or water 600 in the pouch 598 is sufficient to spread heat laterally so that the heat is uniformly distributed across the bandage 594 and across its lower surface 595.

Figure 18:
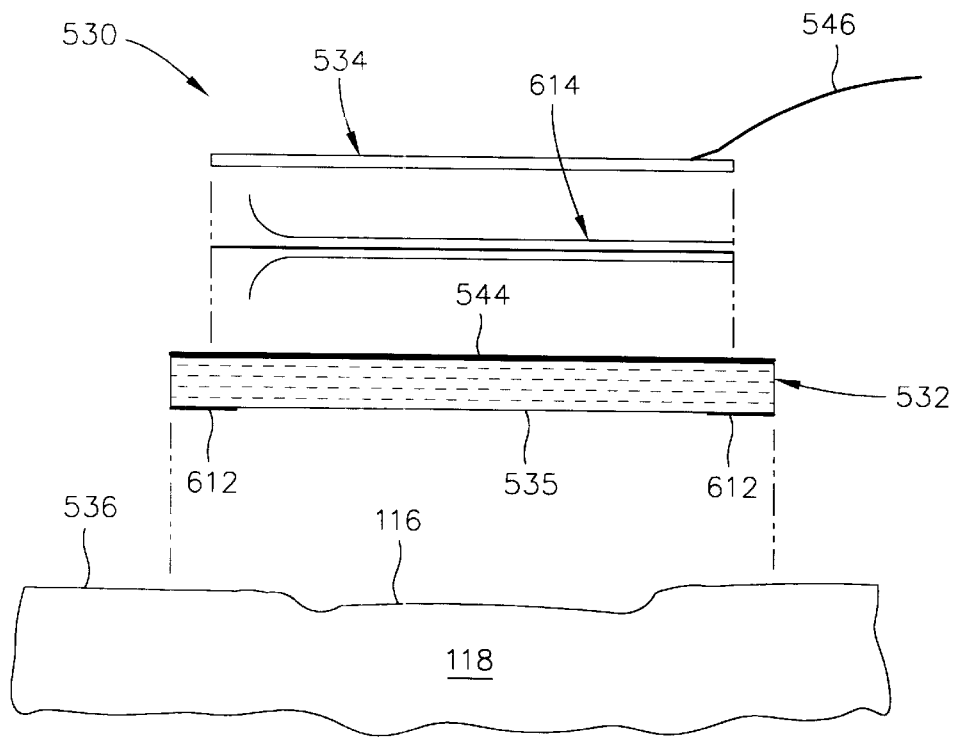
FIG. 18 is an exploded cross-sectional view of a wound treatment apparatus showing double-sided tape employed for affixing a heater to the FIG. 13 embodiment.

FIG. 18 is an exploded illustration of the wound treatment apparatus 530 shown in FIG. 13. The bandage 532 and the heater 534 are highly flexible; in the figure, they are planar and in a non-flexed condition. The lower surface 535 of the bandage 532 is provided with a pattern of adhesive material at 612 around its periphery for adhering the bandage 532 to the person's body 118. When attached to the person's body, the pattern of adhesive material retains moisture at the wound treatment area. The heater 534 may be attached to the polymeric film 544 of the bandage by double-sided tape 614. The pull strength of the double-sided tape 614 may be less than the pull strength of the pattern of adhesive material 612 so that the heater 534 can be removed without removing the bandage 532 from the person's body.

Figure 19:
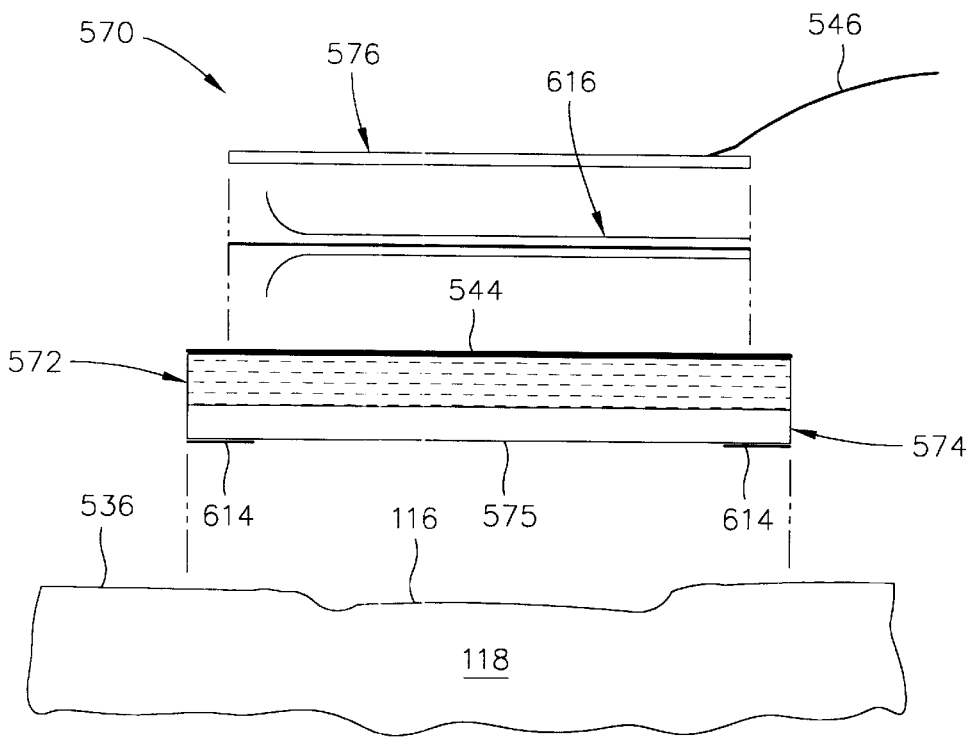
FIG. 19 is an exploded cross-sectional view of a wound treatment apparatus showing double-sided tape employed for affixing a heater to the FIG. 16 embodiment.

FIG. 19 is an exploded illustration of the wound treatment apparatus 570 in FIG. 16. The bottom surface 575 of the bandage 574 is provided with a pattern of adhesive 614 around its periphery for attaching the bandage 574 to the person's body. The pattern of adhesive material retains moisture at the wound treatment area, when the bandage is attached. The heater 576 is attached to the heat spreading layer 572 by a double-sided tape 616 as described hereinabove. Again, the pull strength of the double-sided tape 616 may be less than the pull strength of the pattern of adhesive material 614 so that the heater 576 can be removed from the heat spreading layer 572 without removing the bandage 574 from the person's body.

Figure 20:
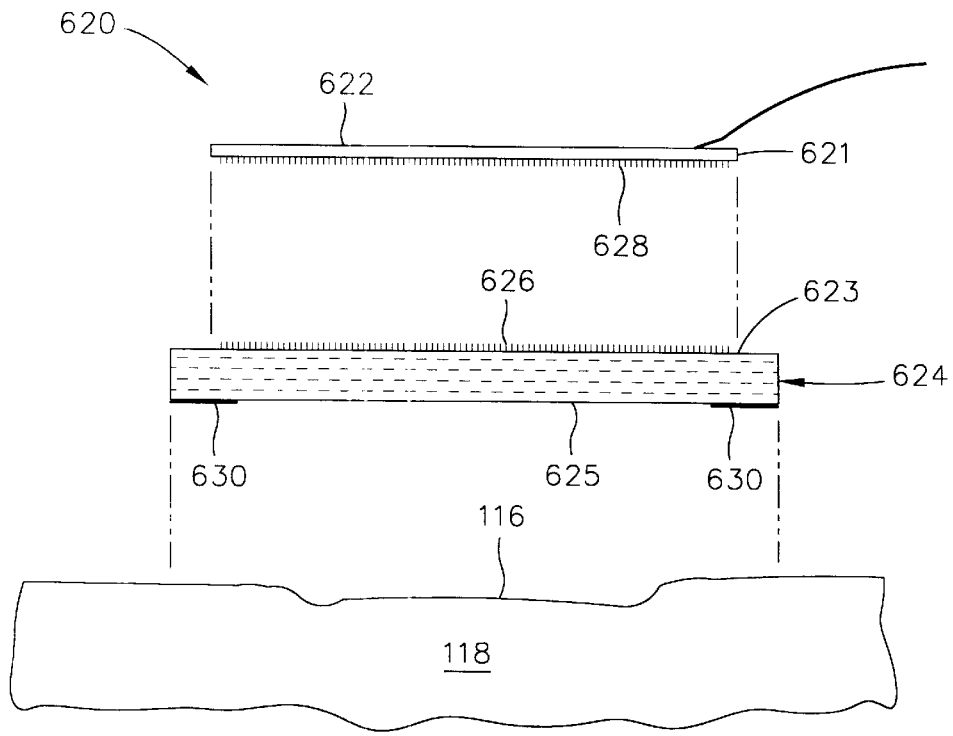
FIG. 20 is a cross-sectional exploded view of a wound treatment apparatus showing another embodiment for affixing a heater to a bandage.

FIG. 20 shows an exploded illustration of a wound treatment apparatus 620 which employs a modified attachment device for attaching the heater 622 to a thermally conductive flexible bandage 624. The bandage 624 is the same as the bandage 532 in FIG. 13 except the polymeric film 544 is replaced by hook-and-eye material 626. The bottom surface 621 of the heater 622 is also provided with hook-and-eye material 628 so that the heater 622 can be easily attached to the bandage 624. The hook-and-eye material will inherently have minute gaps and may have additional larger gaps because of the depression of the wound 116. However, the bandage 624 is provided with a thermally conductive material that is thick enough to spread heat laterally within the bandage 624 so as to distribute heat uniformly from its upper surface 623 to its lower surface 625 as shown in FIG. 12. The lower surface 625 of the bandage 624 may have a pattern of adhesive material 630 with greater pull strength than the hook-and-eye material 626/628. The pattern of adhesive material 630 retains moisture at the wound treatment area.

Figure 21:
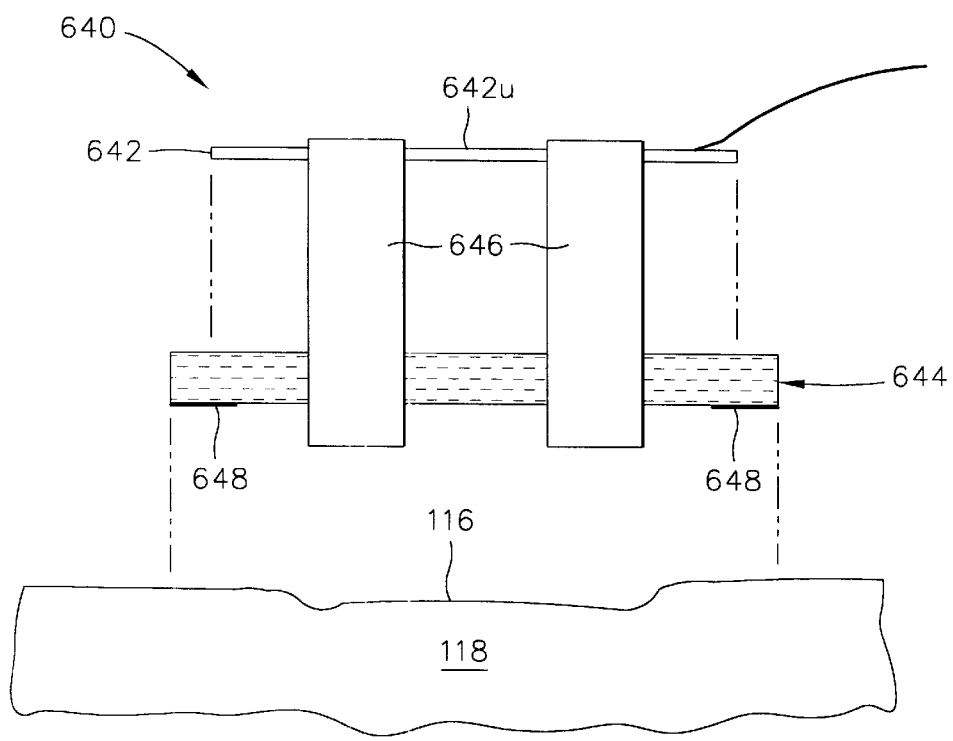
FIG. 21 is a cross-sectional exploded view of a wound treatment apparatus showing a further embodiment for affixing a heater to a bandage.

FIG. 21 shows an exploded illustration of a wound treatment apparatus 640 which employs another device for attaching a heater 642 to a bandage 644. The bandage 644 is the same as the bandage 532 in FIG. 13 except the polymeric film 544 may be omitted. In this embodiment adhesive tabs 646, which extend from the upper surface 642u of the heater 642, are employed for attaching the bandage 644 to the person's body 118. The heater 642 can then be removed by pulling the tabs 646 from the person's body. If a pattern of adhesive material 648 is employed about the bottom periphery of the bandage 644, the bandage 644 will remain in place when the heater 642 is removed. If the pattern of adhesive material 648 is omitted, the entire heat treatment apparatus 640 can be removed upon pulling the tabs 646 from the person's body. Alternatively, the tabs 646 may be adhesively attached to the bandage 644. In this case, the polymeric film 544 in FIG. 13 and the body adhesive 648 should be employed.

Figure 22:
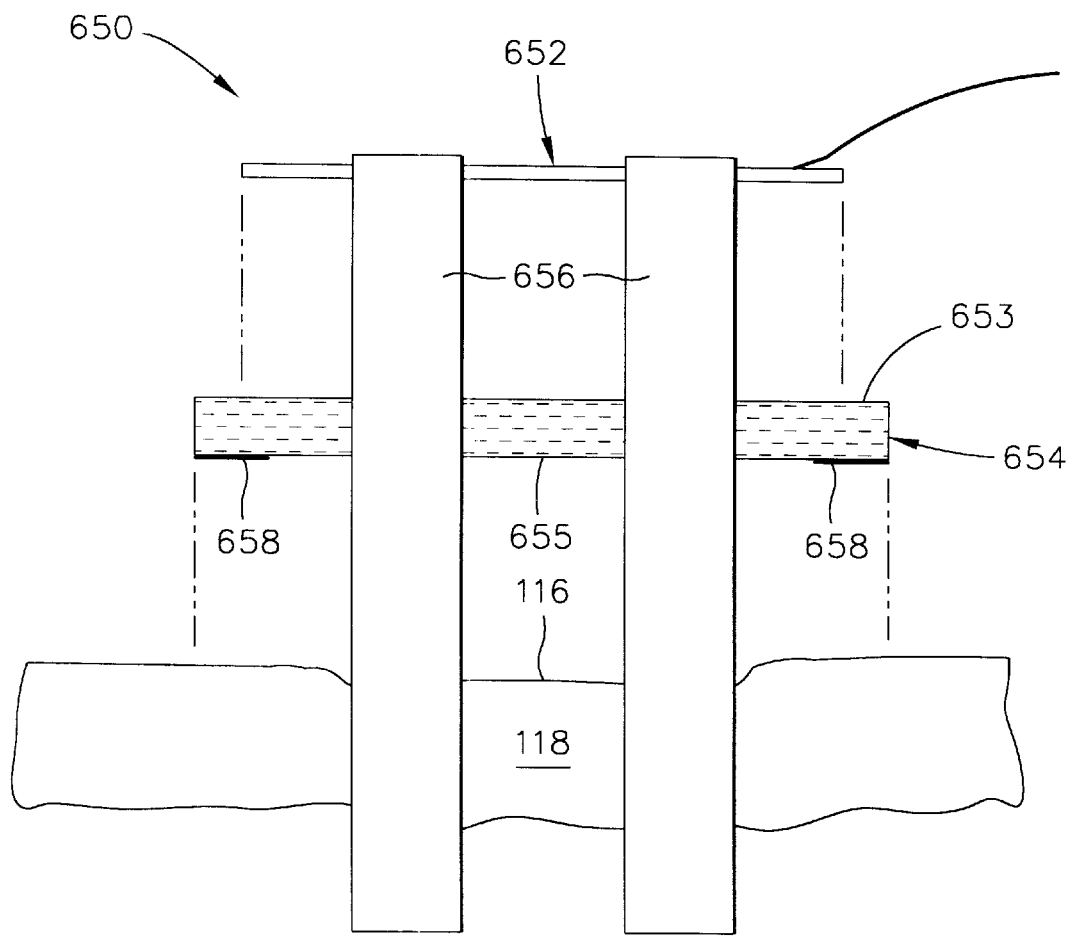
FIG. 22 is a cross-sectional exploded view of a wound treatment apparatus showing a still another embodiment for affixing a heater to a bandage.

FIG. 22 shows an exploded cross-section of a heat treatment apparatus 650 which employs a still another attachment device for attaching a heater 652 to a bandage 654. In this embodiment, the straps 656 extend completely around the person's body, such as around a leg or arm, in order to hold the heater 652 against the upper surface 653 of the bandage 654. In this embodiment it is not necessary for the bandage 654 to have a polymeric film on its upper surface. If the lower surface 655 of the bandage 654 is provided with a pattern of adhesive material 658 on the periphery of the lower surface 655, the bandage 654 will remain attached to the body upon releasing the straps whereas if the body adhesive material 658 is omitted the entire wound treatment apparatus 650 will be removed upon release of the straps.

Clearly, other embodiments and modifications of this invention will occur readily to those of ordinary skill in the art in view of these teachings. Therefore, this invention is to be limited only by the following claims, which include all such embodiments and modifications when viewed in conjunction with the above specification and accompanying drawings.

What is claimed is:

1. A wound treatment apparatus comprising:
   a bandage, the bandage having first and second surfaces;
   the first surface of the bandage for being depressed into a wound;
   adhesive material on the first surface of the bandage;
   a flexible heat spreading layer having first and second surfaces;
   the heat spreading layer including a thermally conductive layer of a thermally conductive material;
   the first surface of the heat spreading layer being in thermal contact with the second surface of the bandage;
   a heater having first and second surfaces;
   the first surface of the heater being in contact with the second surface of the heat spreading layer over a predetermined wound treatment area; and
   an attachment means for maintaining said contact of the heater with the heat spreading layer.

2. The wound treatment apparatus of claim 1 including:
   control means connected to the heater for controlling the temperature of the heater so that temperature at the treatment area is normothermic.

3. The wound treatment apparatus of claim 1 wherein the heat spreading layer includes:
   a flexible pouch; and
   a thermally conductive fluid in the flexible pouch.

4. The wound treatment apparatus of claim 1 wherein the heat spreading layer includes:

a layer of polymeric film;

the layer of polymeric film and the thermally conductive layer being in contact, with the thermally conductive layer forming the first surface of the heat spreading layer and the polymeric layer forming the second surface of the heat spreading layer; and the attachment means being an adhesive attachment means for maintaining the second surface of the heat spreading layer in contact with the first surface of the heater.

5. The wound treatment apparatus of claim 4 wherein the thermally conductive layer is a hydrogel layer.

6. The wound treatment apparatus of claim 4 wherein the thermally conductive layer is a hydrocolloid layer.

7. The wound treatment apparatus of claim 4 wherein the thermally conductive layer is a polymeric gel layer.

8. The wound treatment apparatus of claim 4 wherein the thermally conductive layer includes a thermally conductive fluid.

9. The wound treatment apparatus of claim 8 including:

control means connected to the heater for controlling the temperature of the heater so that temperature at the treatment area is in a range from 36° C. to 38° C.

10. The wound treatment apparatus of claim 8 including:

the adhesive material on first surface of the bandage having a pattern adapted to contact a person's skin surrounding said wound treatment area.

11. The wound treatment apparatus of claim 10 including:

each of the adhesive attachment means and the pattern of adhesive material having a pull strength; and the pull strength of the adhesive attachment means being less than the pull strength of the pattern of adhesive material.

12. The wound treatment apparatus of claim 8 wherein the heater includes an electrical resistance element.

13. The wound treatment apparatus of claim 12 wherein the electrical resistance element is configured for providing heat only in a central region of the treatment area.

14. The wound treatment apparatus of claim 12 wherein the electrical resistance element is configured for providing heat only in a peripheral region of the treatment area.

15. The wound treatment apparatus of claim 8 wherein the adhesive attachment means is a double-sided tape.

16. The wound treatment apparatus of claim 8 wherein the bandage and the heat spreading layer are joined by a common layer.

* * * * *